US00PP24166P3

(12) United States Plant Patent
Olesen

(10) Patent No.: US PP24,166 P3
(45) Date of Patent: Jan. 21, 2014

(54) MINIATURE ROSE PLANT NAMED 'POULPAH054'

(50) Latin Name: ***Rosa* hybrid**
Varietal Denomination: Poulpah054

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 55 days.

(21) Appl. No.: 13/317,262

(22) Filed: Oct. 13, 2011

(65) Prior Publication Data

US 2013/0097748 P1 Apr. 18, 2013

(51) Int. Cl.
*A01H 5/00* (2006.01)

(52) U.S. Cl.
USPC ..... Plt./118

(58) Field of Classification Search
USPC ..... Plt./118
See application file for complete search history.

(56) References Cited

PUBLICATIONS

GTITM UPOVROM Citation for 'Poulpah054' as per QZ PBR 20100221; Feb. 3, 2010.*

* cited by examiner

*Primary Examiner* — Kent L Bell

(57) ABSTRACT

A new miniature rose plant that has abundant, yellow flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpah054'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2006 and the resulting seeds were planted in a controlled environment in Fredensborg, Denmark. The new variety, named 'Poulpah054', originated as a single seedling from the stated cross.

The new variety may be distinguished from its female seed parent primarily by flower color. The female seed parent has light yellow flowers while the new variety has yellow flowers.

The new variety may be distinguished from its male pollen parent primarily by the height of the plant. The male pollen parent grows to a height of 15 cm. The new variety is 18 to 25 cm.

The objective of the hybridization of this rose variety for commercial culture was to create a new and distinct variety with unique qualities, such as:

1. Uniform and abundant yellow flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah054' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah054' was selected by the inventor as a single plant from the progeny of the hybridization in 2006.

Asexual reproduction of 'Poulpah054' by cuttings and traditional budding was first done by Mogens N. Olesen in the nursery in Fredensborg, Denmark in June of 2007. This initial and other subsequent propagations conducted in controlled environments have demonstrated that the characteristics of 'Poulpah054' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah054'. Specifically illustrated in the drawing.

DETAILED DESCRIPTION OF THE VARIETY

Figure 1:
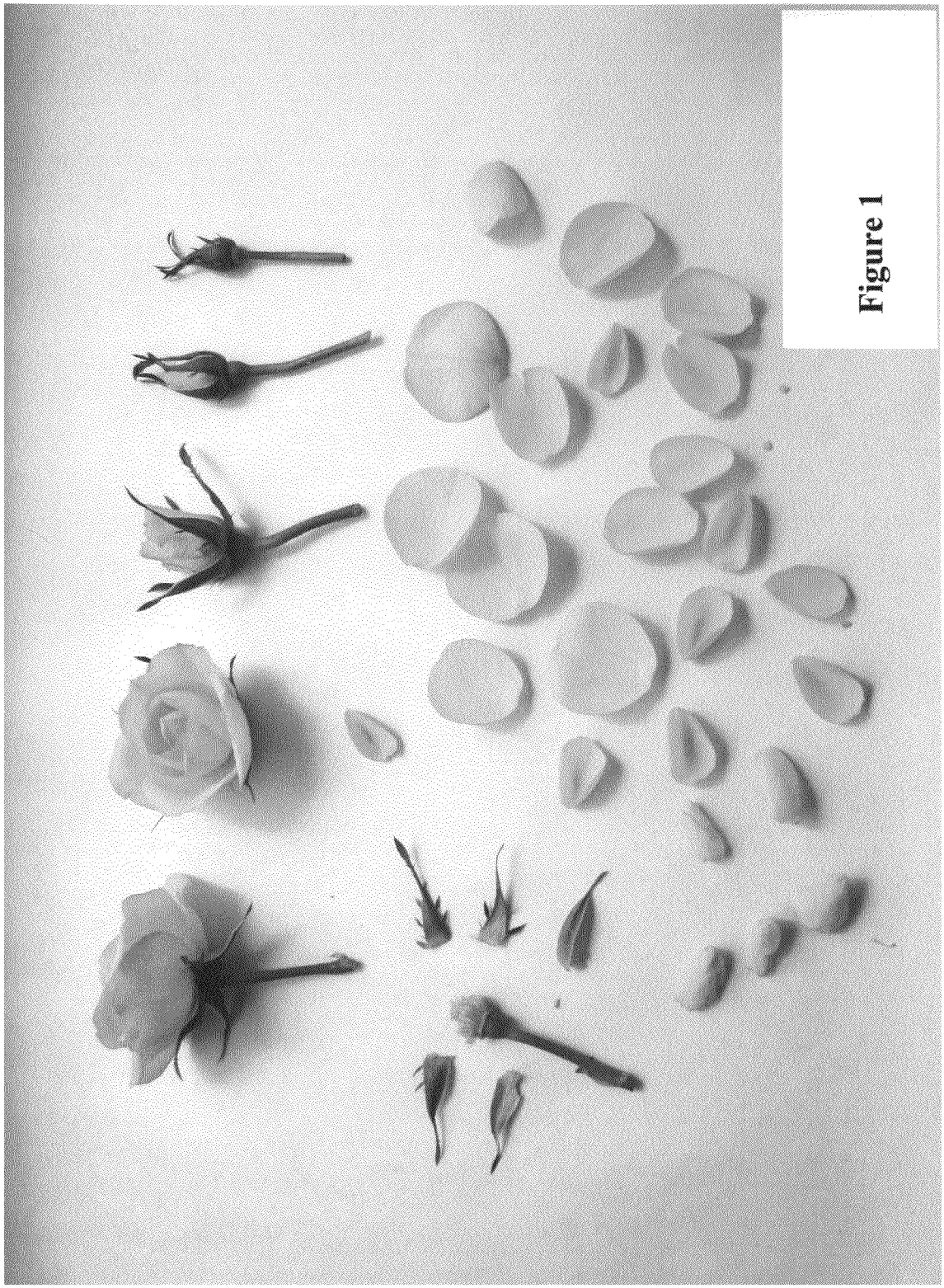
FIG. 1; Open flowers, flower buds, petals detached, and reproductive flower parts.
Figure 2:
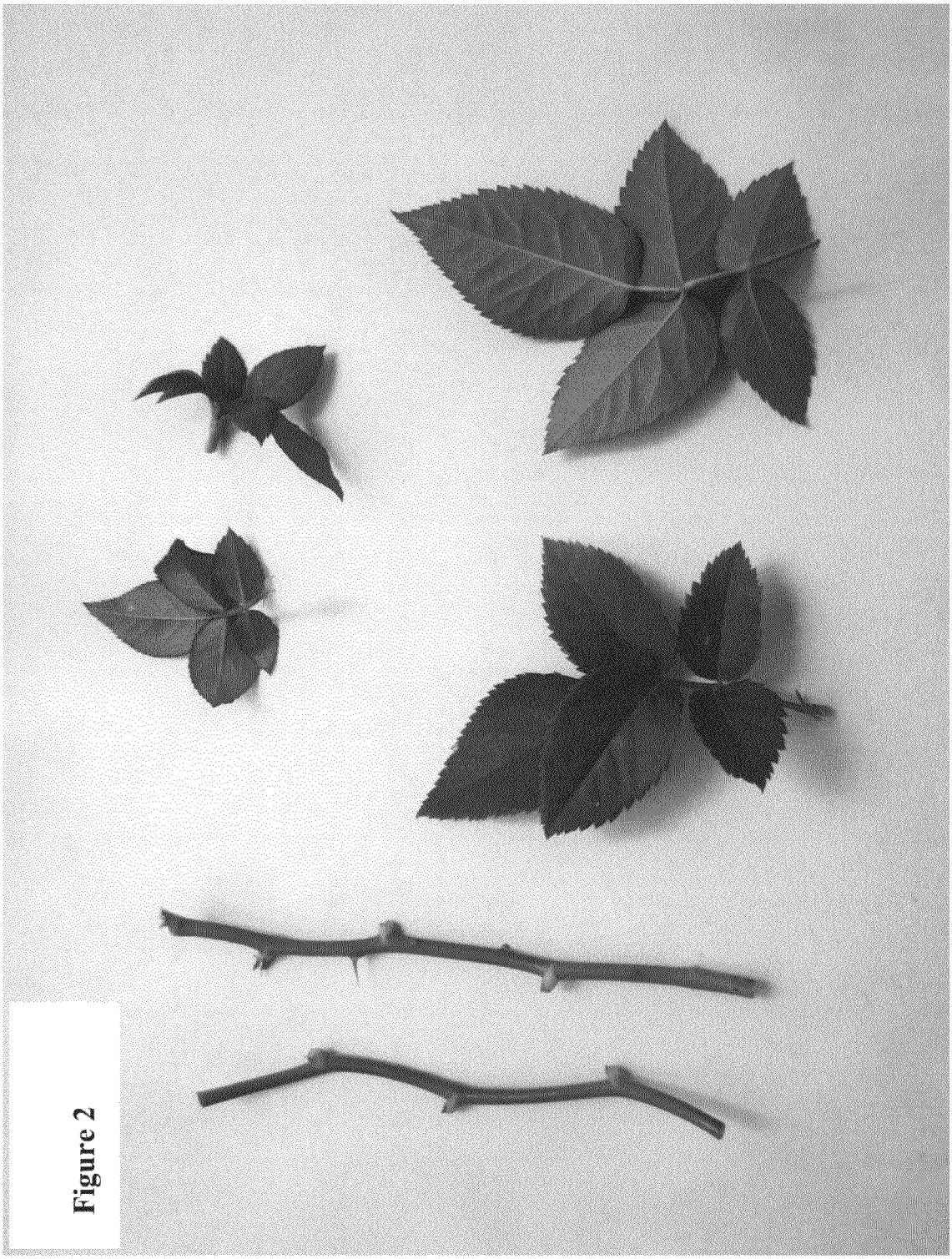
FIG. 2; Leaves and stems.

The following is a description of 'Poulpah054', as observed in its growth in glasshouses in Half Moon Bay, Calif. Observed plants are 10 weeks of age and were cultivated in 10.5 cm pots. Color references are made using The Royal Horticultural Society (London, England) Colour Chart, 2001, except where common terms of color are used.

For a comparison, several physical characteristics of the rose variety 'Poulsun', U.S. Plant Pat. No. 9,716. are compared to 'Poulpah054' in Chart 1.

CHART 1

| | 'Poulpah054' | 'Poulsun' |
|---|---|---|
| Petalage: | 40 | 30 to 35 |
| Flower longevity: | 28 days | 6 days |
| Petal upper side coloration, upon opening: | Yellow Group 13C with intonations of Yellow Orange-Group 15C at margins. | Yellow Group 13A |

FLOWER AND FLOWER BUD

Blooming habit: Continuous.

Flower bud:

*Size.*—Upon opening, 20 mm in length from base of receptacle to end of bud. 10 mm in diameter.

*Bud form.*—Ovate.

*Bud color.*—As sepals unfold petals are Yellow Group 4B with intonations of Yellow-Green Group 145B.

*Sepals.*—Upper Surface: Color: Yellow-Green Group 145B and 147A. At the margins of the apex, Greyed-Purple Group 183A. Texture: Smooth. Lower Surface: Color: Green Group 137A. At the margins of the apex, Greyed-Purple Group 183A. Texture: Smooth. Shape: Apex: Cirrhose. Base: Flat at union with receptacle. Margins: Margins have moderate foliaceous appendages on three of the five sepals. Size: 35 mm long by 10 mm wide.

*Receptacle.*—Surface Texture: Smooth. Shape: Campanulate. Size: 4 mm in height, by 5 mm wide. Color: Yellow-Green Group 144A.

*Pedicel.*—Surface: Somewhat rough with small prickles. Length: 30 to 35 mm. Diameter: About 3 mm. Color: Yellow-Green Group 144B. Strength: Medium strength.

*Borne.*—Singly.

Flower bloom:

*Fragrance.*—Light floral.

*Duration.*—As a pot plant, flowers lastup to 28 days. Petals do not fall cleanly away from plant.

*Size.*—60 to 70 mm flower diameter. 25 mm deep.

*Form.*—Generally, flowers are cupped with a tightly closed center.

*Shape of flower, side view.*—The upper portion is flat. The lower portion is a flattened convex.

Petalage: There are normally 40 petals, 5 to 8 of which are petaloids.

Color:

*Upon opening, petals.*—Outermost petals: Upper Surface: Yellow Group 13C with intonations of Yellow-Orange Group 15C at margins. Lower Surface: Yellow Group 13C with intonations of Yellow-Orange Group 15C at margins. Occasionally, there are streaks of Red Group 47B. Innermost petals: Upper Surface: Yellow Group 13C with intonations of Yellow-Orange Group 15C at margins. Lower Surface: Yellow-Orange Group 14C with intonations of Yellow-Orange Group 16B. Occasional streaks of Red Group 47B. Petal Spots: Upon opening, no distinctive coloration at petal base observed. Outer and inner petals: Upper Surface: Yellow-Orange Group 13B to 13C with intonations of Yellow-Orange Group 15C at margins. Lower Surface: Yellow-Orange Group 13B to 13C with intonations of Yellow-Orange Group 15C at margins. Occasional streaks of Red Group 47B. Petal Spots: After opening, no distinctive coloration at petal base observed.

General tonality: Yellow-Orange Group 14A to Yellow Group 12B.

Petals:

*Petal reflex.*—Absent.

*Petal margin.*—Entire and uniform.

*Shape.*—Generally broad elliptic. Base: Rounded. Apex: Rounded.

*Size.*—35 mm long by 38 mm wide on average. Inner petals are 18 mm long by 20 mm wide.

*Thickness.*—Average.

*Texture.*—Smooth.

Petaloids:

*Quantity.*—Normally, there are 5 to 8 petaloids.

*Size.*—15 mm long; 8 mm wide.

*Shape.*—Apex is acute. Base is acute. Generally the petaloids are asymmetrical.

*Color.*—Upper Surface: Yellow-Orange Group 13B to 13C with intonations of Yellow-Orange Group 15C at margins. Lower Surface: Yellow-Orange Group 13B to 13C with intonations of Yellow-Orange Group 15C at margins. Occasional streaks of Red Group 47B.

Reproductive organs:

*Pollen.*—None observed.

*Anthers.*—Size: 2 mm long. Color: Yellow-Orange Group 16B. Quantity: 60 on average.

*Filaments.*—Color: Yellow Group 12A. Length: 4 mm.

*Pistils.*—Length: 5 mm long. Quantity: On average, 40.

*Stigmas.*—Superior relative to the length of the filaments and the height of the anthers. Color: Greyed-Yellow Group 160A.

*Styles.*—Color: Red Group 39B.

*Seed formation.*—Not observed.

PLANT

Plant growth: Upright. When grown as a 10.5 cm pot plant on its own roots, the average height of the plant itself is 18 to 25 cm and the average width is 15 cm.

Stems:

*Color.*—Young wood: Yellow-Green Group 144B. Older wood: Yellow-Green Group 144A. Internodal distance: 30 mm on average. Length of stems: 15 cm from the base of the plant to the flowering portion.

*Diameter.*—3 to 4 mm.

*Surface texture.*—Young wood: Smooth. Older wood: Smooth.

Prickles:

*Incidence.*—4 per 10 cm of stem.

*Size.*—Average length 6 mm.

*Color.*—Juvenile prickles are Greyed-Red Group 181C. Mature prickles are Greyed-Red Group 181C.

*Shape.*—Linear.

Plant foliage: On average, 5 leaflets.

*Compound leaf size.*—80 mm (l)×75 mm (w).

*Quantity.*—2 leaves per 10 cm of stem.

*Color.*—Juvenile foliage: Upper Leaf Surface: Yellow-Green Group 147A. Lower Leaf Surface: Yellow-Green Group 147B. Anthocyanin: Margins are Greyed-Red Group 183A. Mature foliage: Upper Leaf Surface: Yellow-Green Group 147A. Lower Leaf Surface: Yellow-Green Group 147B.

Plant leaves and leaflets:

*Stipules.*—Size: 9 mm in length. Shape: Linear, slightly broad based with outward extending apecies. Margins: Entire. Color: Yellow-Green Group 147A.

*Petiole.*—Length: 15 mm on average. Diameter: 1 mm. Color: Upper surface is Green Group 138A. Anthocyanin is the color of Greyed-Purple Group 183A. The lower surface is Yellow-Green Group 144B. Underneath: Small prickles observed.

*Rachis.*—Length: About 20 mm. Diameter: About 1 mmm. Color: Upper surface is Green Group 138A. Anthocyanin is the color of Greyed-Purple Group 183A. The lower surface is Yellow-Green Group 144B. Underneath: Small prickles observed.

*Leaflet.*—Size: 55 mm in length by 30 mm wide. Margin: Serrate. General Shape: Elliptical. Apex Shape: Acute. Base Shape: Round. Texture: Smooth. Arrangement: Odd pinnate. Venation: Reticulate. Leaf Gloss: Matte surface.

Disease resistance: Average resistance to powdery and downy mildew, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticultural Society heat zone 7.

The invention claimed is:

1. A new and distinct variety of rose plant of the miniature class named 'Poulpah054', substantially as illustrated and described herein, due to its abundant, yellow flowers, vigorous growth, compact habit, suitability for production from softwood cuttings in pots, and durable flowers and foliage that make the variety suitable for distribution in the floral industry.

* * * * *